United States Patent [19]
Soest et al.

[11] Patent Number: 5,644,392
[45] Date of Patent: Jul. 1, 1997

[54] SCANNING SYSTEM FOR LUMBER

[75] Inventors: Jon F. Soest; James N. Horn, both of Seattle; Thomas E. Lock; Gordon L. Mitchell, both of Woodinville, all of Wash.

[73] Assignee: U.S. Natural Resources, Inc., Vancouver, Wash.

[21] Appl. No.: 527,169

[22] Filed: Sep. 12, 1995

[51] Int. Cl.$^6$ .................................................. G01N 21/00
[52] U.S. Cl. .......................... 356/237; 356/445; 356/446; 250/559.48; 250/559.18
[58] Field of Search .................................. 356/237, 445, 356/446; 250/571, 572

[56] References Cited

U.S. PATENT DOCUMENTS

| | | |
|---|---|---|
| 3,850,526 | 11/1974 | Corey . |
| 3,922,093 | 11/1975 | Dandliker . |
| 3,976,384 | 8/1976 | Matthews . |
| 4,276,910 | 7/1981 | Eickenberger . |
| 4,606,645 | 8/1986 | Matthews . |
| 4,710,642 | 12/1987 | McNeil . |
| 4,939,379 | 7/1990 | Horn . |
| 4,945,253 | 7/1990 | Frohardt . |
| 5,252,836 | 10/1993 | Matthews . |
| 5,311,131 | 5/1994 | Smith . |
| 5,412,220 | 5/1995 | Moore ........................... 356/237 |
| 5,465,152 | 11/1995 | Bilodeau et al. .................. 356/237 |

OTHER PUBLICATIONS

"A Simple Ortical Scanner For Grain Defects", Soest, et al—Oct. 26, 1993.
"Evaluation Of Colour Spaces, et al", Adel, et al.—Oct. 17, 1993.
"Multivariate Image Analysis, et al,"Hagman, et al. —Oct. 25, 1993.

Primary Examiner—Frank Gonzalez
Assistant Examiner—Reginald A. Ratliff
Attorney, Agent, or Firm—Robert L. Harrington

[57] ABSTRACT

A scanning system for wood products to detect grain defects and product geometry simultaneously. Multiple scanner sets cast parallel beams of light at an angle of incidence in a plane that is normal to the surface of the wood product. Scanner sets are provided to scan both the top and bottom surfaces of the wood product. The scanner sets include detector arrays to detect the reflected light of the beams off the surface of the product. One array of each set is positioned strategic to the angle of incidence and another is positioned strategic to the angle of specular reflection. The magnitudes of the detector are compared to determine clear wood or grain defect. The time of detection is used to calculate thickness/geometry.

8 Claims, 3 Drawing Sheets

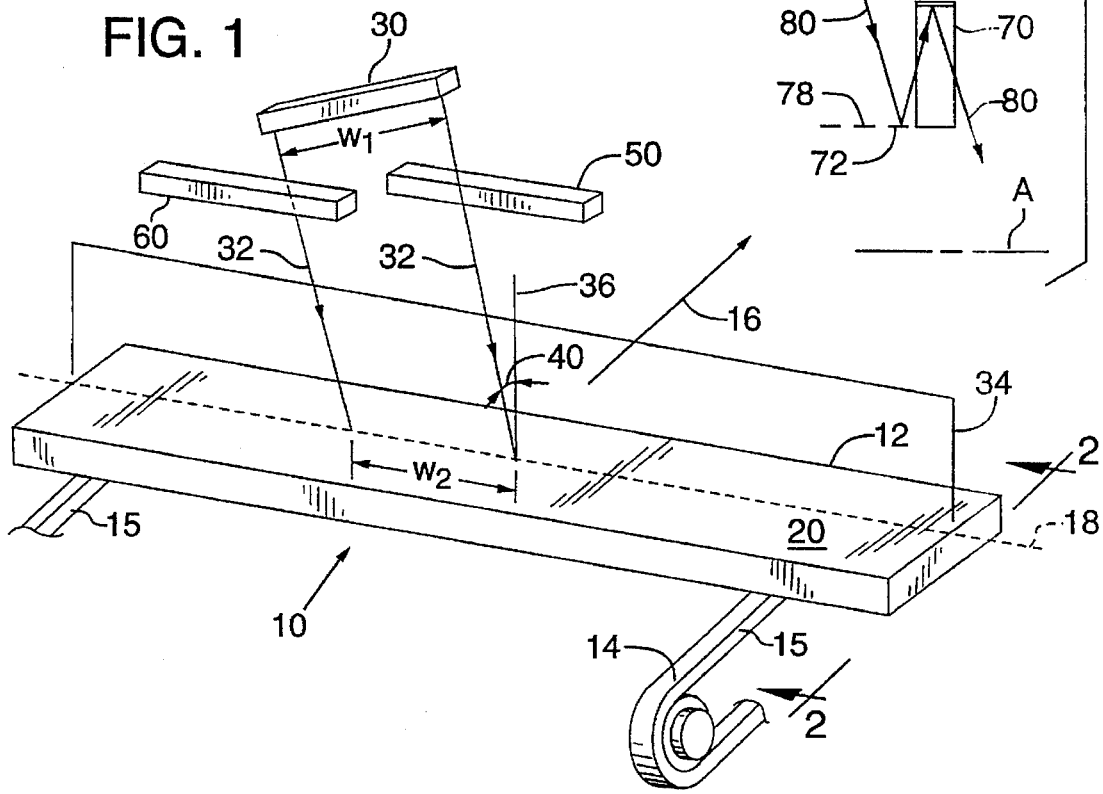
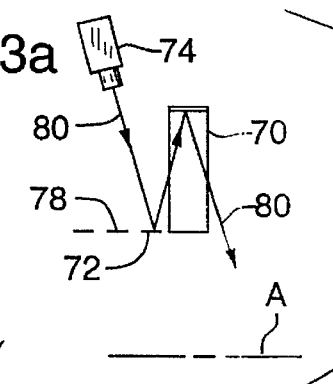
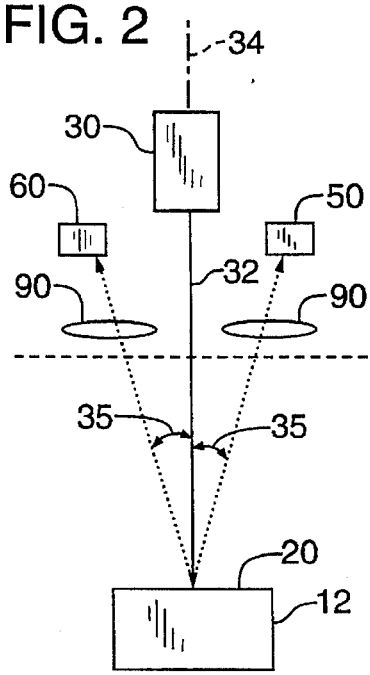
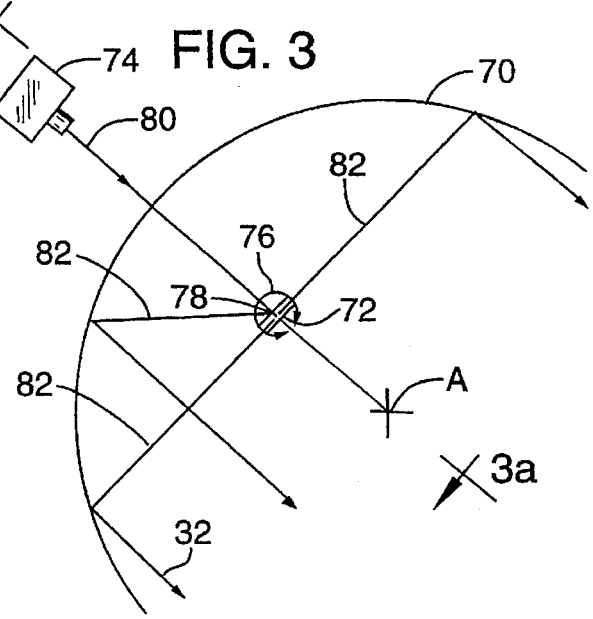

SCANNING SYSTEM FOR LUMBER

FIELD OF THE INVENTION

This invention relates to scanning systems used to identify the geometric configuration of a piece of lumber and/or to detect defects in the lumber, and more particularly to a system that allows defect scanning of an elongated piece of lumber being conveyed transversely and alternatively to also identify its geometric configuration.

BACKGROUND OF THE INVENTION

Scanners, e.g., laser beam scanners, have been used for years to determine the geometric configuration of a piece of lumber, e.g., its height and/or width and/or length. See for example U.S. Pat. No. 4,939,379. More recently such scanners have been used to detect defects in the lumber. See for example U.S. Pat. No. 5,252,836. (The disclosures of these two patents in particular are incorporated herein by reference.)

A limitation of prior geometric scanners is that readings taken for determining dimensions are taken at widely spaced intervals, e.g., 3–6 inch intervals along the length of the lumber. Such limitations are primarily necessitated by crosstalk between adjacent scanner locations but other factors are also involved. A limitation in defect scanning is that such is more successfully accomplished over a narrow width where the elongated lumber pieces are traveling lengthwise along a conveyor. Lumber mill processing almost universally conveys the lumber pieces transversely and adapting the prior known systems to lumber mill processing has not been previously commercially successful to date.

SUMMARY OF THE PRESENT INVENTION

At least three areas of improvement have been developed to produce the preferred system of the present invention. Defect scanning as described in the '836 patent relies on detecting specular and diffuse reflection of a light beam and comparing the light intensity of each. Specular reflection by definition is a light beam that reflects off a planar surface at the same angle at which it is projected onto the surface. A small deviation away from true specular reflection is preferred (which is permitted by the nature of light reflection from wood cells) as it permits a narrow field of sweep scanning as described in the '836 patent. The sweep scanning of the '836 patent allows the use of a single scanner to scan a lumber piece, e.g., of 4 inch width traveling lengthwise, but it does not permit scanning of lumber pieces conveyed transversely, e.g., for pieces 8–20 feet in length, which would require a large number of such scanners.

The present invention provides for a single scanner to perform the function of many scanners. This is accomplished by a technique referred to as telecentric scanning. In a preferred embodiment we use, in combination, a large curved mirror and a pivoting flat mirror (or, e.g., rotating polygon mirror). The pivoting mirror is placed in the path of the laser beam and through reflection produces a sweeping projection of the light beam onto the curved mirror. The position of the pivoting mirror is strategically placed at the focal point of the curved mirror. The reflection off the curved surface of the mirror reflects the beam at every position of the curved surface in a parallel direction. Thus, the curved mirror having a two foot linear span from one end to the other will sweepingly project a light beam in a reciprocating linear light pattern onto the surface of a lumber piece, all at the same angle of incidence. (It will be noted from FIG. 1 that the pattern projected on the lumber piece $W_2$ is slightly larger/wider than the beam scan width $W_1$ due to the angle of projection. Hereafter such projected line is referred to as a parallel linear light pattern or simply linear light pattern. The light from the projected line will reflect off the lumber piece at the same common angle (specular reflection) and detectors can be strategically positioned to intercept the light along a similar two foot span.

The reflected light has heretofore been typically gathered by a single lens and converged onto a plurality of diodes. In the present preferred system, a diode is provided, e.g., for readings at one-fourth inch interval. Thus, a two foot span requires 96 diodes. Also, rather than providing a single gathering lens for the single laser beam projection, multiple lenses are provided with each lens gathering light for impingement onto, e.g., 4 diodes. Thus, the 96 diodes requires 24 lenses. The multiple lenses are desirable for focusing the light beam which is needed for height detection.

Reading of the light intensity signal produced by a diode requires amplification. Multiple sequential diodes cannot be connected to the same amplifier as the signals will be merged and the readings flawed. Whereas the diodes are relatively inexpensive, the amplifiers are not. Thus, the third improvement is the connection to an amplifier of multiple spaced diodes, e.g., every fourth diode in the sequence. Thus, the 96 diodes can be serviced by, e.g., 24 amplifiers. The first amplifier would amplify the signals from diodes 1, 5, etc. The second 2, 6, etc. The important consideration is that the spacings be adequate to allow a definite distinction between adjacent signals and also to avoid overloading the amplifiers which will create an undesirable noise level.

In the system described, a single laser light source projects a single light beam in a constant direction. A pivoting mirror in the path of the light beam converts the steady beam to a sweeping beam onto a curved mirror. The curved mirror projects the sweeping beam as a moving light beam projected consistently at the same angle i.e., in parallel throughout the two foot length of the mirror onto a two foot plus section of a transversely conveyed lumber piece. The reflected parallel light projection is received by two sets of detectors (including lenses, diodes and amplifiers). One set is placed in the path of specular reflection and the other in a path of diffuse reflection. The signals are read and analyzed by a computer.

For determining defects, specular and diffuse reflection from substantially the same location on the lumber are compared. The specular reflection reading will be more intense until a defect passes through the projected light. The specular reflection drops to the level of the diffuse reflection and the computer indicates a defect. The two foot span is, of course, not sufficient for the total lumber piece and multiple scanner systems, e.g., at two foot intervals, are provided for 8, 12, 20 foot long lumber pieces.

The thickness of the lumber is determined by triangulation and time (using the specular reflection readings only). The angles of incidence and reflection are the same. Thus, the only change to the triangle as the thickness changes is the length of the sides and that length can be determined by knowing the position at which the light beam was reflected off the curved mirror, and the position of reception, i.e., the diode that receives the signal. These two positions are identified by time comparisons, i.e., where on the mirror was the beam being projected when the reflection was received by a particular diode. The process will be explained in more detail and the system will be more fully appreciated and understood by reference to the following detailed description and drawings referred to therein.

DESCRIPTION OF DRAWINGS

FIG. 1 is a schematic view in perspective of a transverse scanner of the present invention in operation;

FIG. 2 is a view of the transverse scanner as viewed on view lines 2—2 of FIG. 1;

FIG. 3 is a schematic view of a light source of the transverse scanner of FIG. 1 and FIG. 3A is a section view as taken on view lines 3A—3A of FIG. 3;

DESCRIPTION OF THE PREFERRED EMBODIMENT

Figure 4:
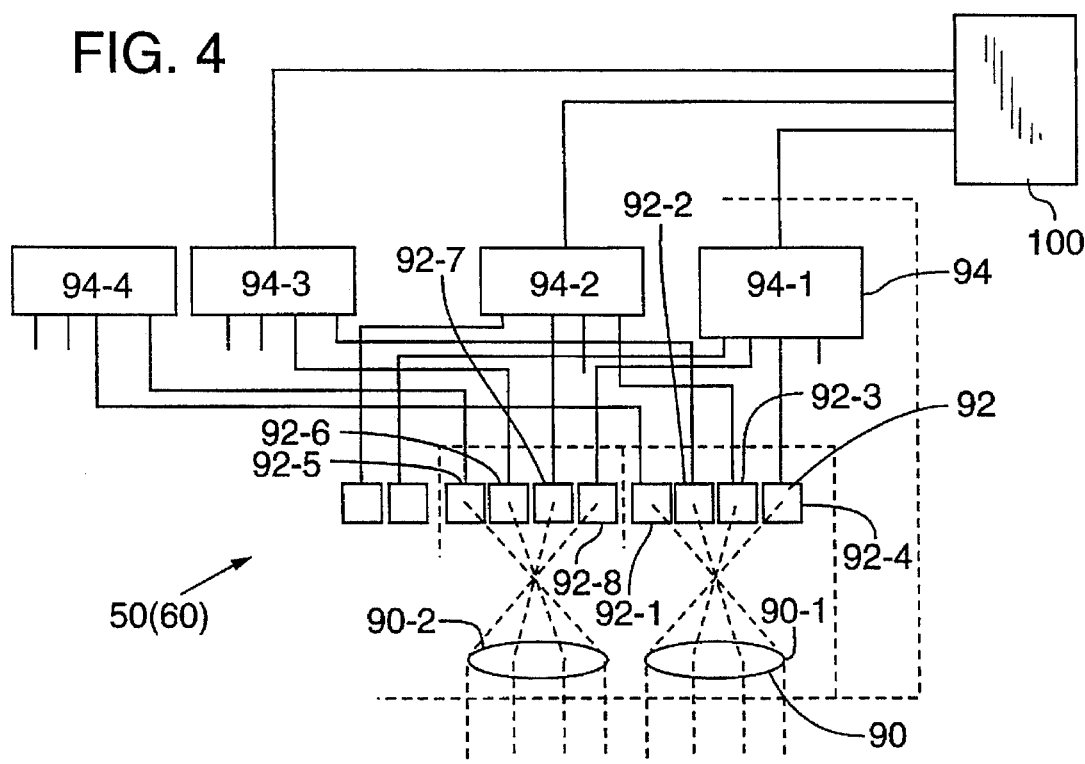
FIG. 4 is a schematic partial view of a detector set of the transverse scanner of FIG. 1.

The transverse scanning apparatus of the present invention relies on the light reflective properties of a wood surface to determine grain defects and/or height variations of the wood product. Basically a scanner casts parallel light beams, e.g., laser beams, at a consistent angle of incidence, onto the wood product surface generally along the normal grain direction of the wood product. The light which is reflected off the wood product surface is sensed or detected by sensor arrays. One of the sensor arrays is positioned strategic to the specular reflection angle of the light projected onto the surface of the wood product. Another sensor array is positioned strategic to the angle of incidence of the light projected on the surface of the wood.

FIG. 1 schematically illustrates one embodiment of a transverse scanning apparatus 10 of the present invention. Products 12 that are to be scanned are conveyed by a known conveyor 14, such as a chain type, at a controlled or measured rate of travel. The wood products 12 are conveyed by the conveyor 14 in the direction indicated by the arrow 16. The longitudinal axis of the wood product 12 is indicated by the dash line 18 and the longitudinal axis of the wood product 12 is normal to the travel direction indicated by arrow 16. The grain direction of the wood product 12 lies generally parallel to the longitudinal axis 18.

Figure 7:
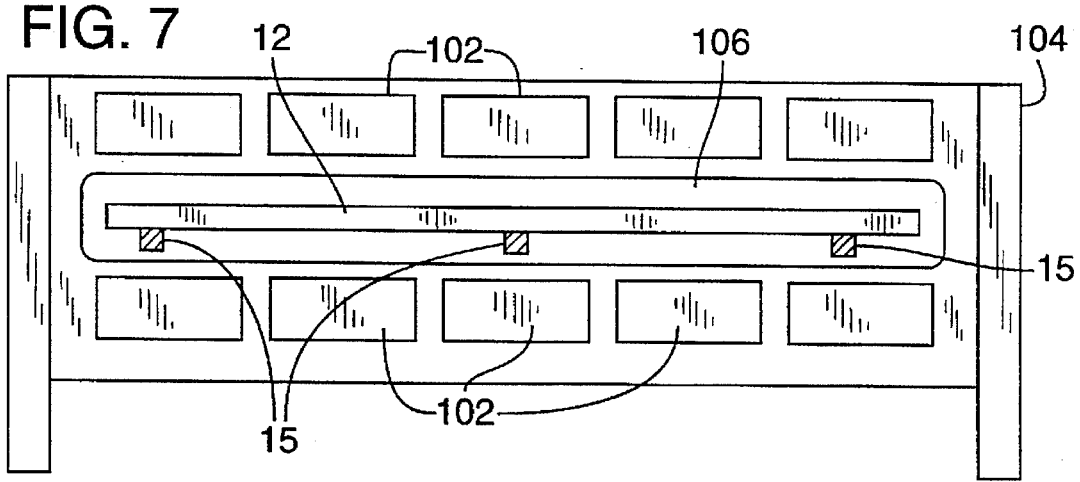
FIGS. 7 and 8 are side and top views illustrating the arrangement of sets of scanners to scan both top and bottom surfaces of the full length of a product.
Figure 8:
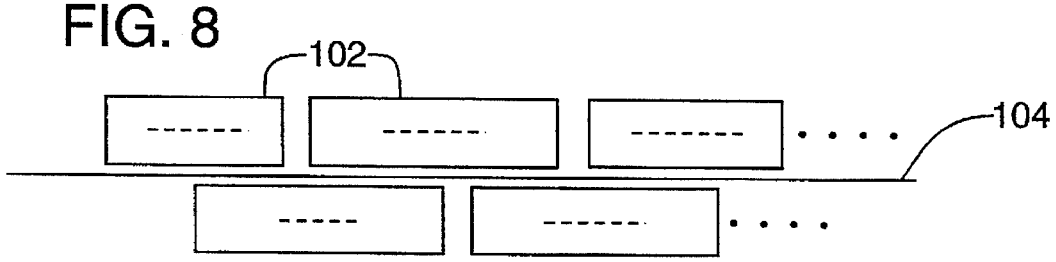

Only one scanner and one set of detector arrays are shown in FIG. 1 for purposes of illustration. In practice, multiple sets of scanners and detector arrays are provided to scan both the top and bottom surfaces of the wood product 12 which is illustrated in FIGS. 7 and 8.

Referring again to FIG. 1, the wood product 12 as it is conveyed by conveyor 14 passes under a light beam generator 30 such as a telecentric flying spot scanner. The light beam generator 30, which will later be further described and illustrated, progressively projects parallel beams 32 of light onto the surface 20 of the wood product 12. The beams 32 of light are cast onto the wood product 12 along the longitudinal length of the wood product and in this embodiment the beams 32 from the light generator 30 having a width $W_1$ of, e.g., two feet will cast a light pattern $W_2$ onto the board of just over two feet depending on the angle of incidence. The beams 32 of the projected light lie in a plane 34 that is substantially normal to the surface 20 of the wood product 12 and the travel direction of the wood product as indicated by arrow 16. The beams 32 will be cast onto the surface 20 of the wood product 12 at an angle of incidence indicated by the numeral 40. The angle 40 is measured from a normal axis 36 which lies in the plane 34.

Detector arrays 50 and 60 are strategically positioned in relation to the light beam generator 30 to detect the reflected light resulting from the beams 32 being cast on the surface 20 of the wood product 12. Detector array 50 is positioned strategic to the specular reflection angle of the beams 32 and detector array 60 is positioned strategic to the angle of incidence of the beams 32. The detector arrays 50 and 60, as best seen in FIG. 2, are offset from the plane 34 at a slight angle 35 to avoid obstruction of the scan beams 32 and to provide clearance for the necessary supporting structure. As described in U.S. Pat. No. 5,252,836, it may be preferable in any event to offset the array 50 to avoid the peak intensity of the specular reflection. The angle of offset 35 for each array 50, 60 is the same and is exaggerated in the drawing for illustrative purposes.

FIGS. 3 and 3A schematically illustrate the arrangement of the light beam generator 30. The light beam generator 30 utilizes a circular mirror 70 (a concave reflective surface in the form of a segment of a cylinder having an axis A), a pivoting or rotating mirror 72, e.g., a rotating polygon mirror, and a light source 74. The pivoting mirror is positioned at the focal point, half the distance between the mirror 70 and the cylindrical axis A. The pivoting mirror 72 is controllably pivoted about an axis 78 (as indicated by the bi-directional arrow 76). The light source 74 directs a ray of light, such as a laser beam 80, onto the surface of the pivoting mirror 72. The pivoting mirror 72 as it pivots will reflect the beam 80 onto the circular mirror 70. The pivoting mirror 72 will pivot through a range as indicated by arrow 76 such that the beam 80 will be progressively reflected along the arc length of the mirror 70, the progressive reflection being represented by beams 82. The beams 82 will reflect off the circular mirror 70 in parallel (or more accurately in near parallel). The circular mirror 70 will progressively and repetitively reflect laser beams 32 in a near linear pattern onto the surface 20 of the wood product 12 indicated by reference $W_2$ in FIG. 1. The laser beams 32 are illustrated in the figures as being in a spaced attitude, when in reality the laser beams 32 are a singular light beam that sweeps across the linear width $W_2$. The depiction in the figures is provided for illustrative purposes to more clearly describe the invention.

A portion of the detector arrays 50 and 60 are schematically illustrated in FIG. 4. The arrays 50 and 60 are arranged to detect the reflected linear light beam pattern (represented by rays 32) off the surface 20 of the wood product 12. In this embodiment, the arrays 50 and 60 are arranged to detect the reflection at about ¼ inch increments. The arrays 50 and 60 as illustrated in FIG. 4 each have multiple lenses 90 to focus the reflected light on light sensing diodes 92. In this embodiment, each light detecting array 50 and 60 has twenty-four lenses 90 and each lens 90 will have four light sensing diodes 92 associated therewith. (Note, however, that this arrangement can be varied.) Thus, a lens designated as 90-1 will have light sensing diodes designated as 92-1, 92-2, 92-3 and 92-4. Similarly lens designated as 90-2 will have light sensing diodes 92-5, 92-6, 92-7 and 92-8. Whereas the lenses are illustrated in the drawing to be parallel to the surface 20 of lumber piece 12, it may be desirable to orient these lenses perpendicular to the light rays 52, 62 (See FIG. 6).

The light sensing diodes 92 are coupled to amplifiers 94. In this embodiment, four amplifier 94 are provided for each detector array 50,60 to amplify the signals from the light sensing diodes 92. The light sensing diodes 92 associated with each lens 90 is coupled to a different amplifier 94. Light sensing diode 92-1 is coupled to the amplifier 94-4, light sensing diode 92-2 is coupled to the amplifier 94-3, light sensing diode 92-3 is coupled to amplifier 92-2 and light sensing diode 92-4 is coupled to amplifier 94-1. Each of the amplifiers 94 (i.e., 94-1, 94-2, 94-3 and 94-4) are coupled to a computer or logic circuit 100. (Although not shown or described, the person skilled in the art will be aware that the amplifier output is converted to digital word via an A/D converter before being coupled to a computer. Further, the term computer hereafter encompasses comparitors such as an analog or digital logic circuit. The description in general assumes this and similar applications of knowledge known to the art.)

The coupling of the light sensing diodes 92 associated with each lens 90 to separate amplifiers permits discrimination of the signals of the light sensing diodes 92. Light sensing diode 92-5 associated with the lens 90-2 is coupled to the amplifier 94-4, light sensing diode 92-6 is coupled to the amplifier 94-3, the light sensing diode 92-7 is coupled to the amplifier 94-2 and the light sensing diode 92-8 is coupled to the amplifier 94-1. The balance of the light sensing diodes 92 associated with each of the lenses 90 are similarly coupled to the amplifiers 94 to provide separation and discrimination of each signal from the light sensing diodes 92.

Operation

Figure 6:
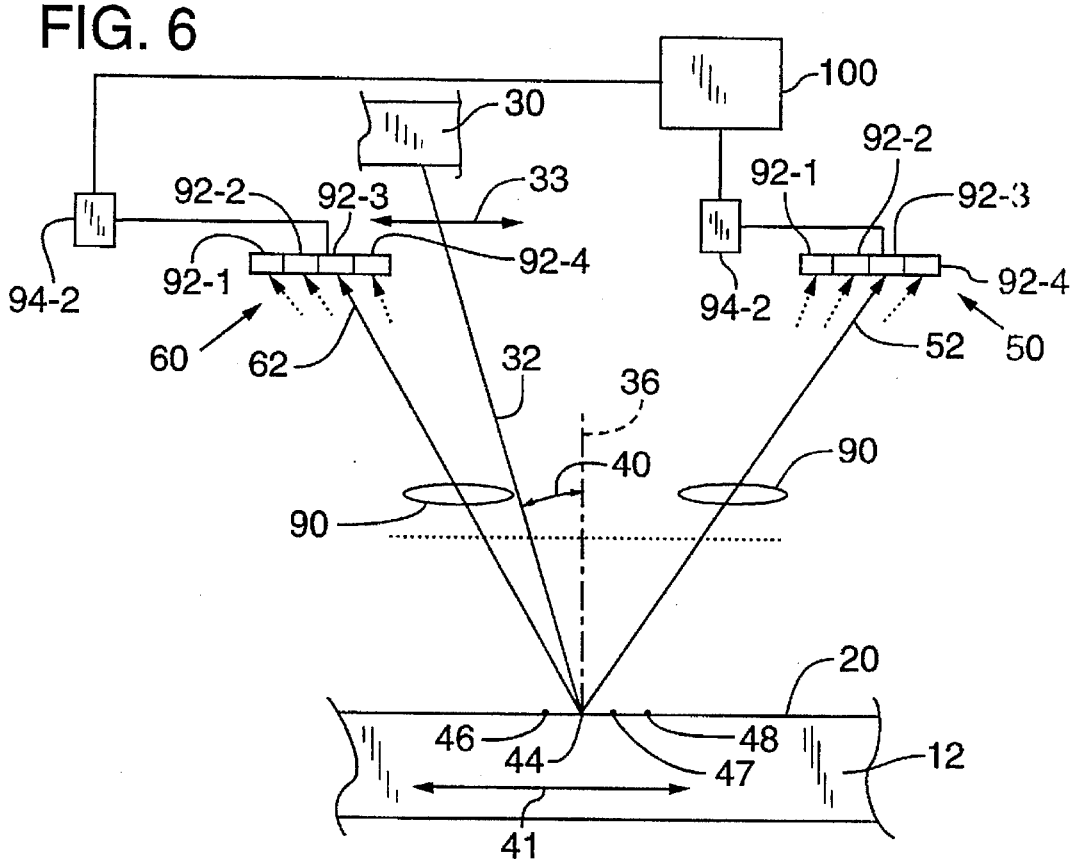
FIG. 6 is a view illustrating the angular relationship of the light source and the detectors of the transverse scanner of FIG. 1.

FIG. 6 shows a beam 32 being cast on the surface 20 of a wood product 12. The beam 32 is cast on the surface 20 of wood product 12 at an angle of incidence as indicated by 40. Only a single point of light impingement (represented by beam 32) is illustrated. However, the light beam generator 30 will cast a linear light pattern $W_2$ as previously discussed. The beam 32 will be cast on the surface 20 of the wood product 12 along its longitudinal length and will generally be along the grain direction, the grain direction being indicated by arrow 41. The beam 32 is cast onto a spot 44 on the surface of the wood product 12. Light reflected off the spot 44 will be focused onto a light sensing diode 92 in each of the detector arrays 50 and 60 by the lenses 90. For purposes of illustration, only one lens 90 is shown for each detector array 50, 60 and only the light sensing diodes 92 associated with the lens 90 of each array 50, 60 are illustrated. The range of detector angles through each lens 90 is exaggerated for drawing clarity.

Light reflected from the spot 44 will be focused on and will be sensed by the light sensing diode 92-3 of each detector array 50 and 60 as indicated by lines 52, 62. The output signal from the light sensing diode 92-3 of detector array 50 is input to an amplifier 94-2 of the detector array 50. Similarly the output signal from the light sensing diode 92-3 of detector array 60 is input to an amplifier 94-2 of the detector array 60. The signal from each of the amplifiers 94-2 of detector arrays 50 and 60 are input to the computer 100 for analysis. (In actual practice the two detectors do not see the reflection at exactly the same time. However, the system identifies in one of several ways the most accurate approximation of the actual signals. For example, the system may use the two signals closest in time or it may use a sampling of an average peak height of the diffuse reflection.)

Figure 5A:
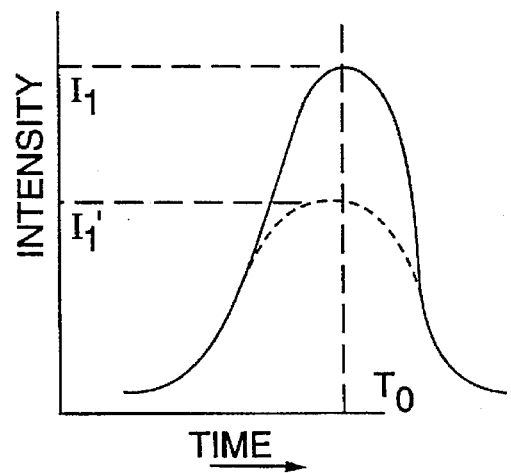
FIGS. 5A and 5B illustrate the signal generated by the scanning system of the invention.
Figure 5B:
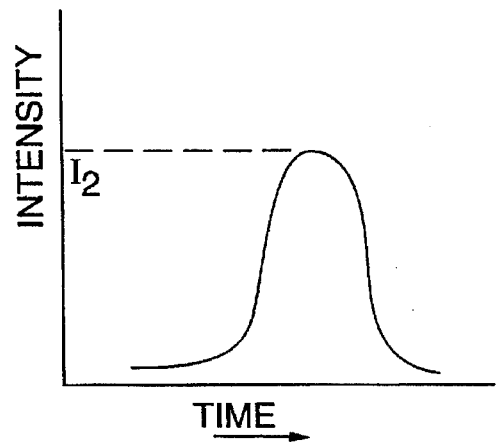

FIGS. 5A and 5B represent the light signal detected by a diode in detectors 50 and 60, respectively. Those skilled in the art will understand that the signal is defined by the lens 90 and by baffling, without which the signal produced would likely be confusing. The computer knows the location of spot 44 because it knows precisely where the beam 32 is being projected (within the field of projection $W_t$ (FIG. 1)) at any instance in time.

The signals of 5A and 5B are compared to determine defects. As noted, the apex $I_1$ of the solid line curve of FIG. 5A is substantially greater than apex 12 of the curve in FIG. 5B. This indicates that the diode of detector array 50 has received a specular reflection indicating a normal wood cell structure. If the signal illustrated in FIG. 5A is like that of the dash line $I_1'$, such indicates diffuse reflection and an abnormal wood cell structure, e.g., a knot wherein the normal grain pattern of the wood surface is interrupted. The basic teaching of diffuse versus specular reflection comparison is described in U.S. Pat. No. 5,252,836.

The signal of FIG. 5A is also used to detect the position of spot 44. The apex $I_1$ is indicated at a precise point in time $T_O$. That is the point where the light beam reflection 52 is essentially centered on the diode, recalling that the beam is sweeping past the diode and thus detects increasing and decreasing intensity as the beam enters and exits that diode. The computer identifies the peak or apex $I_t$ as a pulse. Whereas the computer knows which diode received the signal and its location in the array, and it knows the precise location of the light beam projection 32 at that point in time, and whereas the angle of projection is fixed, the precise position of spot 44 can be determined, i.e., through the process of triangulation. Such readings are taken at one-fourth inch increments as indicated by spots 46, 47 and 48. The collection of the spot locations over the entire surface area 20 establish the configuration of surface area 20, and knowing the configuration of the bottom surface of the board 12 produces the configuration of the total board.

FIGS. 7 and 8 schematically illustrate multiple scanner sets 102 mounted to a frame 104 of the transverse scanner for scanning the total length of a wood product 12. Each scan set 102 includes a light beam generator 30, a detector array 50 and a detector array 60 arranged in the manner previously described. As best seen in FIG. 7, scanner sets 102 are provided on the top and bottom of the frame 104 for scanning both the top and the bottom surfaces of the wood product 12 as the wood product 12 is being conveyed by the conveyor 14. The scan plane of the scanner sets 102 on the top portion of the frame 104 are offset from the scan plane of the scanner sets on the bottom of the frame 104 to avoid interference.

The frame 104 has an opening or window 106 sufficiently large to accommodate the drive chains 15 of the conveyor 14 and the wood product(s) 12 received on the drive chains.

In operation wood products 12 are conveyed by the conveyor 14 at a known rate of travel. The beam generators 30 of the scan sets 102 will cast a beam of light (beams 32) along the top and bottom surfaces along the longitudinal length of the wood product 12. The beams 32 may be cast at select time intervals to provide inspection or sensing criteria at select increments across the width of the product 12. The beams 32 will be cast at time intervals based on the travel rate of the conveyor 14 and the desired spacing between successive beams.

The detector arrays 50, 60 will input data to the computer 100 for each reference point of the top and bottom surfaces of the wood product 12 as to whether or not that reference point indicates clear wood or a grain defect. The computer 100 will process the data to provide a mapping of the wood products surfaces (top and bottom) to detail the presence (if any) of wood grain defects. This data will be used for subsequent processing of the wood product.

Whereas the preferred embodiment includes multiple detectors in the array 60 for the diffuse reflection, unlike the specular reflection, diffuse reflection can be detected over a wide range of angular positions and a single detector may be utilized in some embodiments. Due to the varying intensity that would be detected using a single detector, the electronics would need to be adapted to factor in these intensity differences. In any event, multiple detectors of array 60 is considered preferable.

Those skilled in the art will recognize that modifications and variations may be made without departing from the true spirit and scope of the invention. One example being the use of the system disclosed herein to define the opposed edges of the lumber pieces, i.e., the profile thereof. Also, it will be understood that a light guide, e.g., fiber optics, may be used at the array position and convey light to remote detectors, i.e., the light guide is an extension of the diode. Accordingly, references to diode positions herein encompasses the light guide considered to be an extension of the diode. The person skilled in the art and having reference to the '836 patent will appreciate the need for adjusting the standards for comparing light intensity of the diodes to accommodate height variation of the lumber piece. He will also be aware of differences, electronically, as between the diodes and as between the amplifiers and will provide appropriate corrections. The invention is therefore not to be limited to the embodiments described and illustrated but is to be determined from the appended claims.

We claim:

1. A system for scanning lumber pieces which are conveyed transversely on a conveyor comprising:

a telecentric scanning device converting a sweeping light beam into a linear light beam pattern projected onto a lumber piece whereby the projection of the beam throughout the pattern is at a substantially constant angle of incidence, said linear light beam pattern projected lengthwise onto the lumber piece which is being transversely conveyed along a path of conveyance, a first array of detectors positioned relative to the surface of a lumber piece to receive the specular reflection of the linear light pattern and a second array including at least one detector positioned relative to the surface of the lumber pieces to receive the diffuse reflection of the linear light pattern;

a computer, said first and second array of detectors establishing the intensity levels of the specular and diffuse reflection, respectively, said intensity levels conveyed to the computer for comparison and determination of a defect.

2. A system as defined in claim 1 wherein the telecentric scanning device comprises a concave curved reflecting surface positioned in the path of a sweeping light beam, said curved reflecting surface arranged relative to the sweeping light beam for reflectively projecting the sweeping light beam as a parallel linear light pattern.

3. A system as defined in claim 2 wherein the concave curved reflecting surface is a segment of a cylinder, the sweeping light beam projecting the light onto the surface from a focal point of the curved surface.

4. A system as defined in claim 1 wherein:

a single telecentric scanning device scans a portion only of the length of a lumber piece, a series of telecentric scanning devices in combination scanning the total length of the lumber piece, and first and second arrays of sequentially arranged detectors for each device, said detectors in combination receiving the reflection of the linear light pattern reflected off a lumber piece surface, each array consisting of multiple lenses for gathering and focusing the reflected light, and at least one diode for each lens for receiving light focused by a lens.

5. A system as defined in claim 4 wherein each light sensing diode projects a signal responsive to the intensity of the light, and multiple amplifiers, each amplifier receiving the signals of selected multiple diodes having non-selected diodes positioned between the selected diodes in the sequence of diodes.

6. A system as defined in claim 1 wherein said computer is programmed to also identify at a selected point in time the location of the projected light beam and the diode receiving the specular reflection thereof, said light beam at a known angle of incidence and reflection and said computer thereby determining the position in space of the point of light beam impingement.

7. A system for scanning lumber pieces which are conveyed laterally on a conveyor comprising:

a light source projecting member for projecting a sweeping light beam, a telecentric scanning device converting a sweeping light beam into a linear light beam pattern projected onto a lumber piece whereby the projection of the beam throughout the pattern is at a constant angle of incidence, said linear light beam pattern projected lengthwise onto the lumber piece which is being transversely conveyed along a path of conveyance, an array of detectors positioned relative to the surface of a lumber piece to receive the specular reflection of the parallel linear light pattern;

a computer, said computer responsive to the detectors and identifying as of a specific point in time a location in space of the beam projection and the diode receiving the specular reflection thereof, said angle of incidence of said light beam being fixed and known to thereby enable the computer to calculate the point in space of impingement of said beam on a lumber piece surface.

8. A system as defined in claim 6 wherein the reflected light impinging on the detector is focused by a lens and baffled to produce an increasing/decreasing signal having a peak, said peak detected by the computer as a pulse and determining both intensity and time, said intensity of the signal of the diffuse reflection detector compared to the signal of the specular reflection detector to determine defects in grain structure at the point of projection, and the time of the pulse enabling the computer to determine the position of the light beam projection which coupled with the location of the diode and the known angle of incidence of the light beam projection allows the computer to calculate the point in space of impingement of said light beam projection on the lumber piece.

* * * * *